US006401713B1

(12) United States Patent
Hill et al.

(10) Patent No.: US 6,401,713 B1
(45) Date of Patent: Jun. 11, 2002

(54) APPARATUS AND METHOD OF PROVIDING CONTINUOUS POSITIVE AIRWAY PRESSURE

(75) Inventors: Peter D. Hill, Monroeville; Douglas M. Mechlenburg, Pittsburg, both of PA (US); Mark C. Estes, Sylmar, CA (US)

(73) Assignee: Respironics, Inc., Pittsburgh, PA (US)

( * ) Notice: Subject to any disclaimer, the term of this patent is extended or adjusted under 35 U.S.C. 154(b) by 0 days.

(21) Appl. No.: 09/539,386

(22) Filed: Mar. 31, 2000

Related U.S. Application Data

(60) Provisional application No. 60/132,626, filed on May 5, 1999.

(51) Int. Cl.[7] ................................................ A61M 16/00

(52) U.S. Cl. ............................ 128/204.21; 128/204.18; 128/205.25

(58) Field of Search ....................... 128/200.24, 204.18, 128/204.21, 205.23, 205.24, 205.25, 848

(56) References Cited

U.S. PATENT DOCUMENTS 5,117,819 A * 6/1992 Servidio et al. ....... 128/204.18
5,199,424 A 4/1993 Sullivan et al.
5,522,382 A 6/1996 Sullivan et al.
5,682,878 A 11/1997 Ogden
5,694,923 A * 12/1997 Hete et al. ............. 128/204.18
5,823,187 A * 10/1998 Estes et al. ............ 128/204.23

* cited by examiner

*Primary Examiner*—Glenn K. Dawson
(74) *Attorney, Agent, or Firm*—Michael W. Haas

(57) ABSTRACT

A pressure support system and method in which a gas flow generating system provides a continuous flow of breathing gas at selectable pressure levels. A patient circuit and interface communicate the continuous flow of breathing gas to the airway of a patient. A controller causes the gas flow generating system to provide the continuous flow of breathing gas to the patient at a first pressure level $P_1$ in an initial therapy session. Thereafter, the pressure level of the continuous flow of breathing gas is increased from the first pressure level $P_1$ to a final pressure level $P_2$ over a first predetermined number D of days. More specifically, in one embodiment, the pressure level is incrementally increased by a predetermined incremental amount $\Delta p$ after n therapy sessions taking place on separate days over this first predetermined number D of days. As a result, the current therapy pressure in each therapy session that takes place on separate days following the initial therapy session is incrementally and automatically increased.

30 Claims, 5 Drawing Sheets

APPARATUS AND METHOD OF PROVIDING CONTINUOUS POSITIVE AIRWAY PRESSURE

This application claims the benefit of 60/132,626 filed May 5, 1999.

BACKGROUND OF THE INVENTION

1. Field of the Invention

The present invention pertains to an apparatus and method of providing continuous positive airway pressure to the airway of a patient suffering from congestive heart failure, and, in particular, to an apparatus and method of providing positive airway pressure to the patient according to a treatment regimen in which the level of pressure support is automatically and gradually increased over the course of several days from an initial low pressure to a final pressure.

2. Description of the Related Art

It is known to provide a continuous positive airway pressure (CPAP) therapy to a patient to treat congestive heart failure (CHF). Such a CPAP treatment, which involves delivering a flow of breathing to the airway of a patient at a constant pressure level throughout the patient's respiratory cycle, has been shown to reduce pulmonary edema and heart size for patients suffering from CHF.

It is also known that the CPAP treatment is generally more effective if the CPAP level is initially set to a relatively low level when the patient first starts the therapy and gradually increases over a period of time, generally between 2–4 weeks, each day the CPAP treatment is provided until the final CPAP level is reached. Although this titration process is relatively simple in that it merely involves increasing the CPAP level provided to the patient each day from a low level to the final CPAP level, this mundane pressure changing process is typically required to be performed by a skilled technician trained in the use of the particular CPAP machine prescribed to the patient. It can be appreciated that this conventional approach for daily gradually increasing the CPAP therapy to treat CHF is an inefficient use of a technician's time, especially in light of the fact that the CPAP level is preferably increased each day over a time period lasting as long as a month. This process is further complicated by the increasing number and variety of CPAP devices, requiring the technician to become proficient in the use of a number of different types of pressure support devices in order to be qualified to perform this relatively uncomplicated process.

SUMMARY OF THE INVENTION

Accordingly, it is an object of the present invention to provide a pressure support system to treat CHF that overcomes the shortcomings of conventional pressure support techniques. This object is achieved according to one embodiment of the present invention by providing a pressure support system that includes a gas flow generating system that generates a continuous flow of breathing gas at selectable pressure levels. A patient circuit and patient interface communicate the continuous flow of breathing gas to the airway of a patient. The pressure support system includes a clock source that increments in at least daily time intervals and a controller that controls the pressure level of the flow of breathing gas provided to the patient. More specifically, the controller causes the gas flow generating system to provide a continuous flow of breathing gas to the patient at a first pressure level $P_1$ in an initial therapy session. Thereafter, the controller automatically causes the gas flow generating system to increase the pressure level of the continuous flow of breathing gas to a final pressure level $P_2$ over a first predetermined number D of days. In one embodiment of the present invention, transitioning from the initial pressure level $P_1$ to the final pressure level $P_2$ over D days includes increasing the pressure level by a predetermined incremental amount $\Delta p$ after n days or after n therapy sessions. As a result, the current pressure $P_{current}$ of the continuous flow of breathing gas provided to a patient in a current therapy session following the initial therapy session is greater than a pressure provided in a previous therapy session taking place on a prior day.

It is yet another object of the present invention to provide a method of providing pressure support to treat CHF that does not suffer from the disadvantages associated with conventional pressure support techniques. This object is achieved by providing a method that includes providing a flow of breathing gas to a patient at a first pressure level $P_1$ in an initial therapy session. Thereafter, the method of the present invention automatically increases the pressure of the continuous flow of breathing gas from the first pressure $P_1$ to a final pressure $P_2$ over a first predetermined number D of days so that a current pressure $P_{current}$ of the continuous flow of breathing gas provided to a patient in a current therapy session following the initial therapy session is greater than a pressure provided to such a patient in a previous therapy session taking place on a prior day. This pressure increasing process is automatically repeated every time n days have elapsed or once n therapy sessions have taken place until a final pressure level $P_2$ is reached or until a set number of days D have elapsed.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
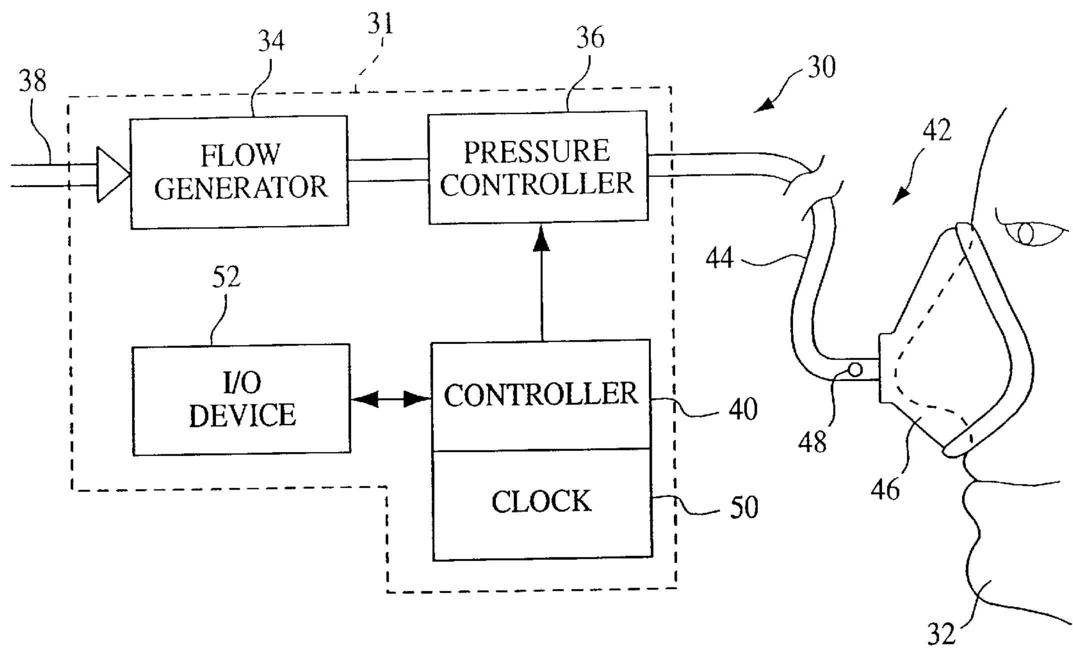
FIG. 1 is a schematic diagram of a pressure support system according to a first embodiment of the present invention.

FIG. 1 schematically illustrates an exemplary embodiment of a pressure support system 30 according to the principles of the present invention. Pressure support system 30 includes a gas flow generating system 31 that provides to a patient 32 a continuous flow of breathing gas at selectable pressures. The term "continuous," as used herein, means that the pressure provided to the patient does not vary based on the patient's respiratory cycle. However, the pressure can be varied over time or over a number of patient breaths during a therapy session so that the patient is presented with different or variable pressures throughout a single therapy session. A conventional CPAP device, such as the SOLO® CPAP System and the Aria® LX CPAP System, both of which are manufactured by Respironics, Inc. of Pittsburgh, Pa., and both of which are capable of varying the pressure provided to the patient during the course of a therapy session are examples of a pressure support device that provides a continuous pressure to the patient at selectable pressure levels. It is to be understood that any pressure support device that provides a ramp type pressure profile, also known as a "soft start", or a delay in providing the pressure, which are typically provided to allow the patient time to fall asleep under a relatively low pressure level are considered to provide a "continuous" flow of breathing gas for purposes of this invention.

In the embodiment of the present invention illustrated in FIG. 1, gas flow generating system 31 includes a flow generator 34 and a pressure controller 36. Flow generator 34 receives a supply of breathing gas 38, which can be oxygen or an oxygen mixture, including air, from any suitable source, such as a pressurized tank of gas or ambient atmosphere. Flow generator 34 elevates the pressure of the breathing gas to generate a flow of such gas. An example of a suitable flow generator is a piston, bellows or a blower. It is to be understood, that flow generator 34 can be eliminated if the supply of breathing gas flow from the gas source is at a sufficient pressure or has a sufficient flow rate so that it does not need an increase in pressure or flow to provide the desired pressure or flow to the patient.

In the embodiment of the present invention shown in FIG. 1, flow generator 34 outputs a flow of breathing gas at a substantially constant predetermined pressure during normal operation. A blower that operates at a constant speed is an example of a device that outputs a flow of breathing gas at a substantially constant predetermined pressure during normal operation. In this embodiment, the flow generating system includes pressure controller 36 to control the final pressure of gas exiting flow generating system 31 and provided to the patient, so that the flow of breathing gas can be supplied to the patient at selectable pressures or flow rates. Examples of suitable pressure controllers include a valve, such as a sleeve or poppet valve, that exhausts gas from the patient circuit or a combination of valves associated with the with patient circuit that arranged to control the pressure in the patient circuit. U.S. Pat. No. 5,694,923 to Hete et al., the contents of which are incorporated herein by reference, discloses an example of a dual poppet valve system suitable for use as pressure controller 36. Pressure controller 36 operates under the control of a controller 40, which is preferably a processor that is capable of receiving data and/or commands and provides a control signal to pressure controller 36 based thereon to cause the desired pressure or flow of breathing gas to be provided to the patient. Controller 40 can be in the same physical housing as flow generator 34 and/or pressure controller 36 or at a location remote therefrom. In the latter case, a suitable communication link and communication protocol must be provided so that the controller can accurately, reliably and securely communicate with the pressure controller.

Pressure support system 30 also includes a patient interface assembly 42 operatively coupled to gas flow generating system 31 to communicate the flow of breathing gas to an airway of patient 32. In the illustrated embodiment, patient interface assembly 42 a patient circuit that carries the flow of breathing gas from the gas flow generator to a patient interface device 46. A typical patient circuit includes a single flexible conduit 44 that couples to the gas flow generating system to carry the flow of breathing gas to the patient interface device. Patient interface device 46 is any appliance, such as a nasal mask, nasal/oral mask, total face mask, nasal cannula, endotracheal tube, or tracheal tube, suitable for communicating a supply of breathing gas to the airway of a patient.

In the illustrated embodiment, patient interface device 46 and/or conduit 44 also include a suitable exhaust port 48 for exhausting breathing gas from patient interface assembly 42 during expiration. Exhaust port 88 is preferably a passive exhaust port in the form of a continuously open port that imposes a flow restriction on the exhaust gas to permit control of the pressure of gas within the patient interface assembly 42, including providing positive end expiratory pressure (PEEP) to the patient. It is to be understood, however, that exhaust port 48 can be an active exhaust port that assumes different configurations to control the rate exhaust from the patient interface assembly depending on its configuration. It is to be further understood that other components, such as a heater, humidifier, temperature sensor, pressure sensor, flow sensor, humidity sensor, capnometer, bacteria filter, microphone or other device that measures, monitors, adjusts and/or controls the flow of gas to the patient or that monitors the patient, can be provided in or connected to the flexible conduit.

In the illustrated embodiment, controller 40 in gas flow generating system 31 includes a clock 50 that measures at least daily time increments. Clock 50 can be built into controller 40 or separate therefrom so that it functions independent of the operation of controller 40. In the embodiment of the present invention where time is measured based on the actual time, and not the time relative to the operation on the pressure support system, it is preferable that clock 50 have a dedicated power supply so that the clock will continue to run even when the pressure support system is off to keep an accurate time measurement.

The timing functions of clock 50 can also be accomplished using a clock source, rather than an actual clock. For example, there exist nationwide clock signals, such as global positioning system (GPS) signals, radio frequency signals, and information provided on computer networks, such as the world wide web, that provide a clocking function. These signals can be used by the pressure generating system as a clock source to measure the elapse of time or the amount of time of operation of the pressure support system. The present invention also contemplates using any of these clock sources to check and/or maintain the accuracy of clock 50.

Gas flow generating system 31 further includes an input/output device 52 that communicates with controller 40 so that data and or commands can be provided to the controller. In addition, the controller can provide information to the user. Examples of suitable input/output devices include switches, a keypad, dials, a touchscreen, and LCD or LED displays. The present invention also contemplates that information can be communicated between the controller and a remote control device, either wirelessly or via a hardwire to allow for remote operation and/or control of the pressure support system.

Figure 2:
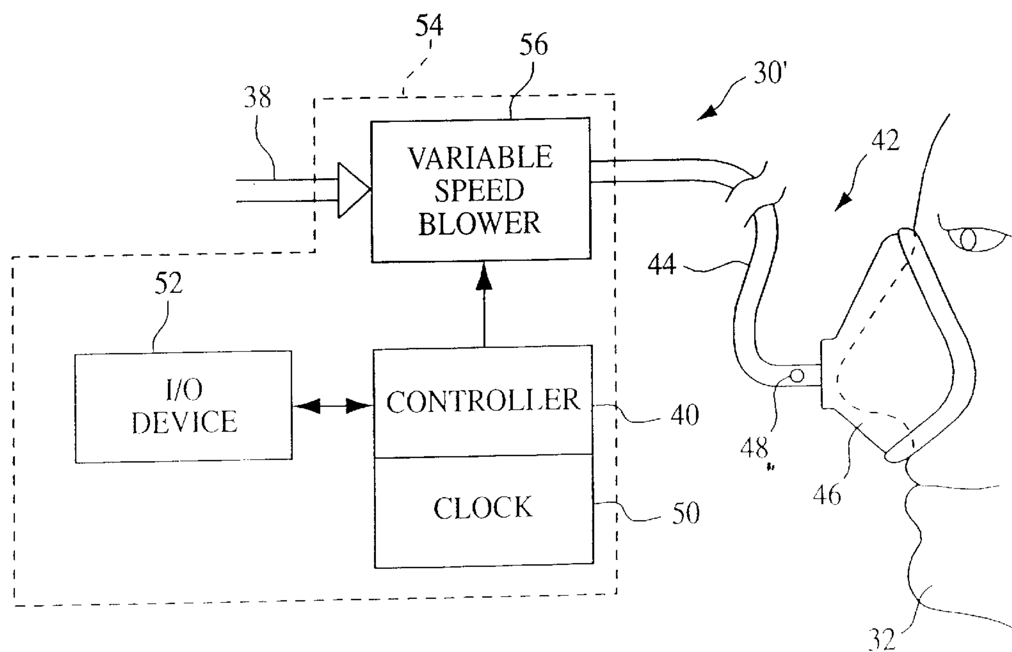
FIG. 2 is a schematic diagram of a pressure support system according to a second embodiment of the present invention.

A slightly different alternative embodiment of a pressure support system 30' according to the principles of the present invention is illustrated in FIG. 2. The primary difference between pressure support system 30' of FIG. 2 and pressure support system 30 of FIG. 1 is in the configuration of the gas flow generating system. In the embodiment of FIG. 2, gas flow generating system 54 does not include a separate flow generator and pressure controller, as is the case with gas flow generating system 31 of FIG. 1. Instead, the two functions performed by the flow generator and pressure controller are performed by a single variable speed blower 56, which includes a variable speed motor driving a blower. Controller 40 controls the speed of the motor, thereby directly controlling the speed of the blower, and, hence, the pressure of the flow of breathing gas output by the gas flow generating system, i.e., without the need for additional pressure or flow control elements in the patient circuit.

It is to be understood, that the present invention contemplates providing one of more feedback elements in patient interface assembly 42, pressure controller 36, flow generator 34 or variable speed blower 54 that provide a feedback signal to controller 40 so that the controller can accurately control the pressure or flow of gas provided to the patient. For example, a flow transducer that measures the flow of breathing gas to the patient, such as a mass flow sensor, for example, or a pressure transducer that measures the pressure of breathing gas in patient interface assembly 42, such as a pneumatach device, for example, can be used to measure and control the pressure or flow of the gas provided to the patient with great accuracy. The use of a feedback device to control or regulate the pressure and/or flow of a gas to a patient is believed to be well known, and, therefore, the details of such a control system are omitted from the present description of the invention for the sake of brevity.

The technique in which a flow of breathing gas is delivered to a patient at varying treatment pressure levels, which vary over a number of days, to treat CHF is described below with reference to FIGS. 3 and 4. As noted above, the controller regulates the pressure of the flow of breathing gas provided to the patient. To treat CHF, controller 40 causes gas flow generating system 31 or 54 to output a continuous pressure during each therapy session. Normally, a therapy session takes place at night while the patient sleeps. During the course of the therapy session, the patient is provided with a continuous positive airway pressure at a current pressure level $P_{current}$. According to the present invention, controller 40, as programmed by I/O device 52, automatically increases the current pressure level $P_{current}$ to be applied to the patient during each therapy session so that the pressure applied to the patient on one day is slightly higher by a predetermined incremental amount $\Delta p$ than the pressure applied to the patient on the previous day. In short, the controller automatically increases $P_{current}$ by a predetermined amount over a number of daily therapy sessions.

Figure 3:
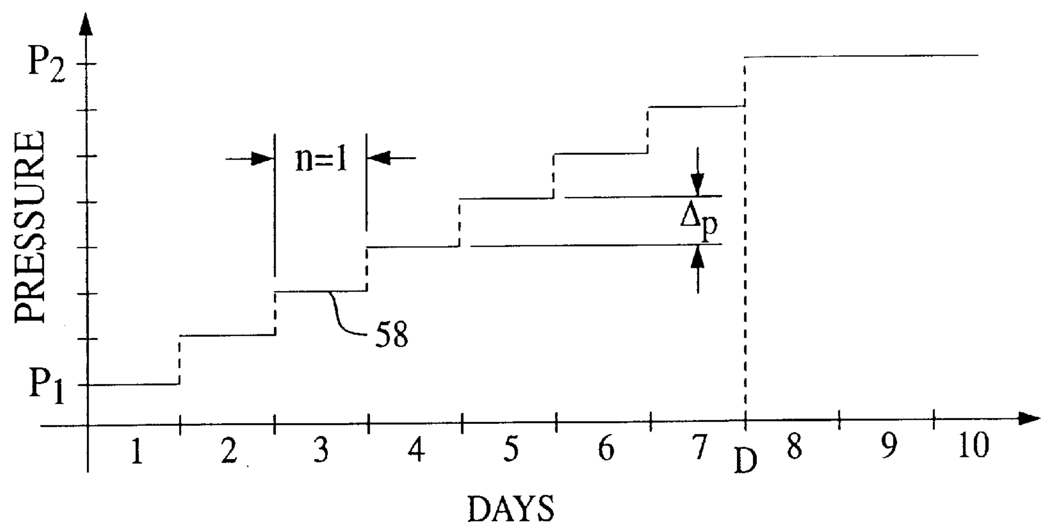
FIGS. 3 and 4 are waveforms illustrating examples of the pressure changes provided by the pressure support system of the present invention.
Figure 4:
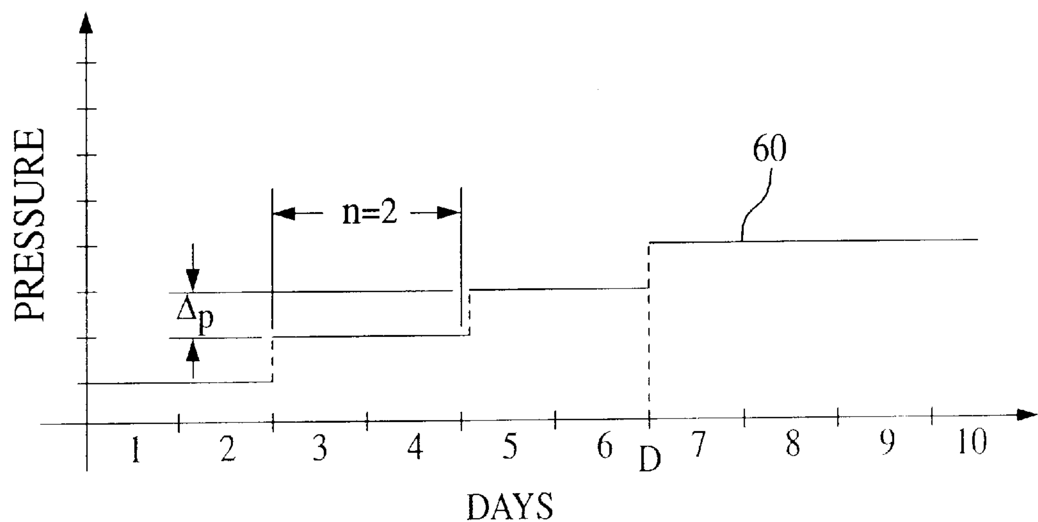

FIG. 3 illustrates an example of how the controller automatically changes the pressure provided to the patient according to the present invention. In this figure, waveform 58 illustrates the current pressure $P_{current}$ provided to the patient during successive therapy sessions, where a new therapy session takes place each day. Although FIG. 3 appears to show the therapy session taking place throughout the entire day, it is to be understood that in most cases, the therapy session only takes place for at least several hours each night.

The treatment regimen begins with the patient being provided a continuous positive pressure $P_1$ in an initial therapy session on day one (1). After a predetermined number n of days, the controller increments the pressure level provided to the patient by an amount $\Delta p$, so that in the next therapy session following the elapse of this predetermined number of days, the current pressure level $P_{current}$ is increased by incremental amount $\Delta p$. In FIG. 3, n is equal to 1 day, so that the gas flow generating system increases the pressure provided to the patient in each therapy session taking place on subsequent days. In FIG. 4, n is equal to 2 days, so that the gas flow generating system increases the pressure provided to the patient in therapy sessions that take place after two days have elapsed. As shown in FIGS. 3 and 4, the controller continues to increase the pressure provided to the patient every n days until either a total number of days D pass or until the pressure provided to the patient reaches the final pressure $P_2$.

The present invention contemplates that the values for the initial pressure $P_1$, final pressure $P_2$, number of days n after which the pressure is increased by an incremental amount, the total number of days D over which the pressure transitions from initial pressure $P_1$ to the final pressure $P_2$, and the incremental amount $\Delta p$ can be set or altered manually via the input/out device or automatically. Allowing these variables to be set manually provides a great degree of flexibility in setting and controlling the pressure versus days/therapy sessions curve so that relatively large number of different curves can be provided to the patient. Setting one or more, or even all of these parameters in advance, however, greatly simplifies the operation of the pressure support device.

In a preferred embodiment of the present invention, the pressure curve provided to the patient is as shown in FIG. 3, which is a generally linear, stair-step curve 58, wherein the pressure provided to the patient increases by an incremental amount $\Delta p$ each day, i.e., each therapy session if the therapy sessions take place on separate days, and the amount of each incremental increase remains constant during the duration D in which the pressure is increased from the initial pressure $P_1$ to final pressure $P_2$. This curve can be set in advance. In addition, the starting and final pressures and/or duration D can be set in advance or set for each patient. It should be further understood, that the number of days n and the incremental amount $\Delta p$ need not remain constant over the course of the pressure increasing time period so that other curves, such as an exponential, square root, or sine curve, can be provided.

Figure 5:
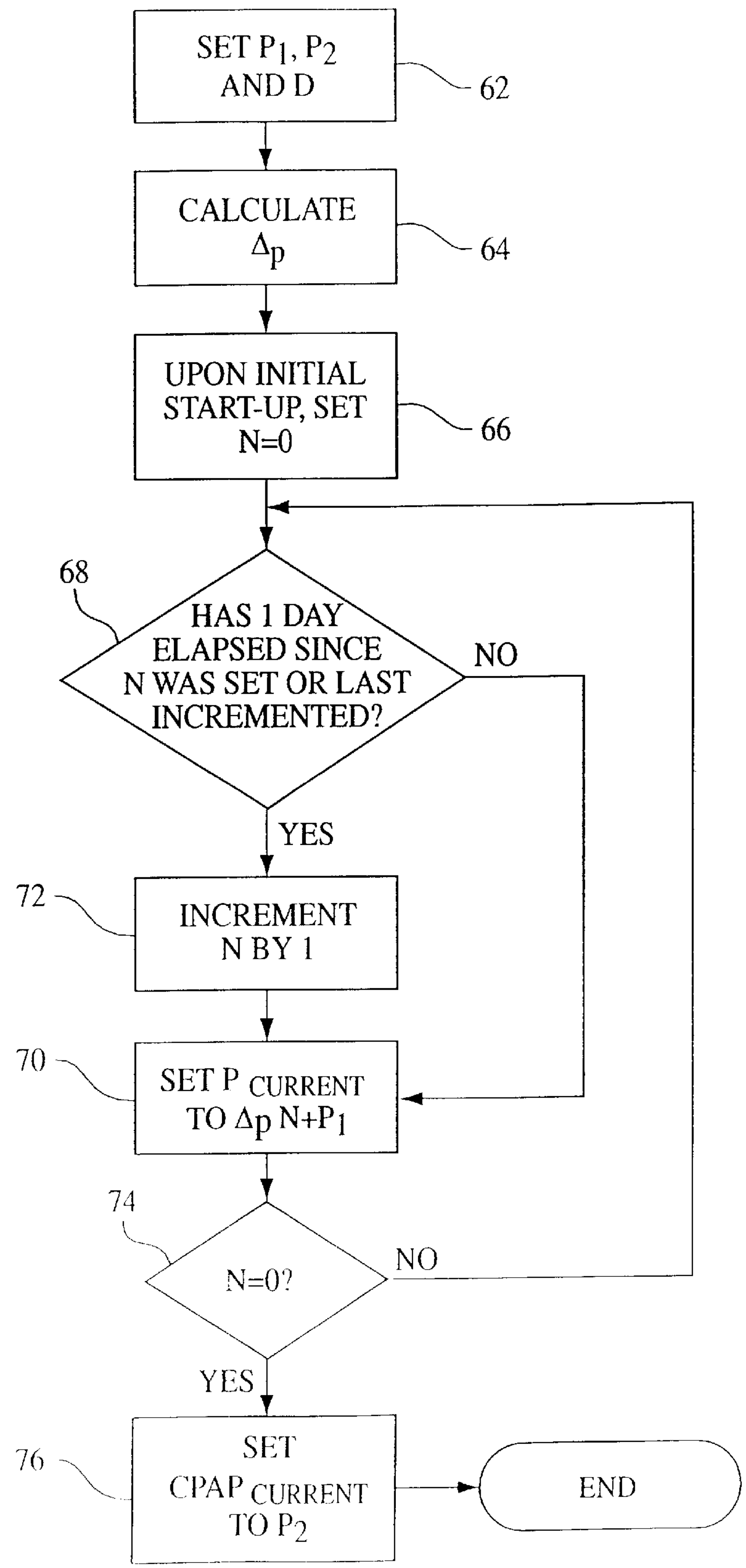
FIG. 5 is a flow chart illustrated an example of the operation of the pressure support system of the present invention.

FIG. 5 illustrates an example of how the present invention provides the pressure curve 58 of FIG. 3. In step 62, the manufacturer, user, or caregiver sets the initial pressure $P_1$, final pressure $P_2$ and the number of days D over which to increment the initial pressure level $P_1$ to the final pressure level $P_2$ In a preferred embodiment of the present invention, these parameters are entered into the controller via input/output device 52 by the caregiver. Thereafter, the controller and/or input/output device are locked out to prevent unauthorized changing of these parameters. In step 64, the controller calculates the incremental amount $\Delta p$ as follows:

$$\Delta p=(P_2-P_1)/D. \tag{1}$$

Next, when the pressure support system is first started to begin the pressure therapy sessions to treat CHF, i.e., at the first therapy session, controller 40 sets a counter N to zero (0) in step 66.

In step 68, controller 40 determines from clock source 50 whether one day has elapsed since N was last set or last incremented. It can be appreciated that the number of days that have elapsed since N was last set or last incremented corresponds to the number of days n after which the pressure was increased by an incremental amount. This number n can be varied depending on the shape of the pressure curve desired. The linear pressure versus days curve 60 in FIG. 4, for example, can be achieved if the controller determines in step 68 whether two (2) days have elapsed since N was last set or last incremented (n=2). It should be noted that predetermined number n need not be an integer, and it can be less than one if the pressure increase is to take place more frequently than on a daily basis. For example, if the pressure increase is to take place every 12 hours, n can be set to 0.5.

If one day has not elapsed since N was last set or last incremented, the controller sets the pressure to be provided to the patient by the gas flow generating system $P_{current}$ in step 70 as follows:

$$P_{current}=\Delta p*N+P_1. \quad (2)$$

If, however, it is determined in step 68 that at least one day has elapsed since N was last set or last incremented, N is incremented by 1 in step 72. Thereafter, the controller sets the current pressure level $P_{current}$ to be provided to the patient in step 70. Because N was incremented by one in step 70, the pressure provided to the patient if one day has elapsed, is increased by one incremental amount Δp. In step 74, the controller determines whether N, which is a running count of the number of days since the therapy was initiated, corresponds to D, which is the total number of days over which the pressure was to be increased from the initial pressure to the final pressure. If N does not equal D in step 72, the above-described process repeats beginning at step 68. If N equals D, the pressure delivered to the patient is thereafter set to $P_2$ in step 76. In an alternative embodiment of the present invention, controller determines whether $P_{current}$ set in step 70 corresponds to $P_2$, in addition to or in place of determining whether N=D, because the present invention contemplates terminating the gradual daily increase in therapy pressure if the total number of days D has elapsed or if the final pressure $P_2$ is reached.

In yet another alternative embodiment of the present invention, the controller uses actual dates to keep track of the succession of days following initiation of the pressure support therapy. In this embodiment, controller 40 in step 66 reads the current date from clock 50 and sets this date as day zero. Then, in step 68, the controllers reads the clock each time the pressure support device is turned on and determines whether the current day is the same as the day set in step 66. If so, the current pressure $P_{current}$ is not incremented from the previous value. If the current date is the next day, assuming n was set to 1 day as shown in step 68 in FIG. 5, the current pressure $P_{current}$ is determined by incrementing the previous pressure by one incremental amount. Thereafter, each time the system is actuated, the controller determines if the current date is one day greater than the previous day, and, if so, increases the current pressure by one incremental amount until the final pressure $P_2$ or total number of days D is reached. Of course, if n is set to less than one, i.e., 0.5, the controller determines if the current time/date is at least 12 hours later than the previous time a therapy session was initiated.

Steps 62–66 are preferably performed the first time the pressure support is operated so that the initial pressure $P_1$, final pressure $P_2$, total number of days D, and incremental amount Δp are established, and to set the incremental count N to zero. Steps 68–76 are preferably performed each time the pressure support system is operated, with the clock continually running even if the pressure support system is not activated so that the running count of the number of days since the start of the therapy is not lost. Performing steps 68–76 only at the time the pressure support system is turned on, i.e., at the start of each therapy session, ensures that an incremental increase in the therapy pressure is not provided to the patient while the patient is using the pressure support system, which can arouse the patient if the change in pressure is abrupt.

The present invention also contemplates that steps 68–76 are continuously performed, so that when the pressure support system is turned on, it immediately determines the current pressure $P_{current}$ to provide to the patient. However, this may result in the controller determining that a pressure increase should be made while the system is being used. For example, if the turn over time elapses while the machine is in use, the machine may try to increase the pressure at that time, which may be disturbing to the patient. The present invention takes this scenario into consideration and optimizes patient comfort should this happen by causing the pressure to change gradually over a number of minutes or by delaying the pressure increase until the next time the unit is on.

Because the pressure support system of the present invention is intended for use at night while the patient sleeps, the determination of when to increment N, i.e., when a day or some other number of hours has elapsed so that the pressure level should be increased (step 68), need not be based on a twenty-four hour cycle from the date of initial start-up as described above with respect to FIG. 5. Instead, the running count of the number of days or hours since the initial start up can be incremented at a set time each day, preferably a time when the pressure support device is typically not in use. For example, one embodiment of the present invention contemplates incrementing N each day at 12:00 pm (noon) and recalculating the current pressure $P_{current}$ either at that time or when the device is turned on later that night, so that the patient is provided with an incrementing pressure each night the device is used. As noted above, if the pressure support system happens to be in use at the time when the a pressure increase is to take place, the pressure increase can be made at that time in a slowly increasing ramp fashion over a number of minutes, or the pressure increase can be delayed until the pressure support unit is off and back on, so that the incremental increase does not take place until the next time the unit is on.

While the invention has been described above as incrementing the pressure provided to the patient on a daily basis by defining the predetermined number n in terms of days, it is to be understood, that other time period measurements, such as hours, minutes or seconds can be used to measure the elapse of time for purposes of increasing the pressure provided to the patient over a relatively long period of time, i.e., several days. For example, instead of a 2 $cmH_2O$ increment of the pressure every day (24 hours), the pressure can be incremented 1 $cmH_2O$ every 12 hours or 0.5 $cmH_2O$ every 6 hours, and so on. Thus, n can be measuring using any time indicator, e.g., days, hours, minutes, seconds, so long as the automatic ramp function of the current pressure $P_{current}$ takes place over a number of days.

The present invention also contemplates that the pressure provided to the patient can be incremented each time a therapy session take place, regardless of whether the therapy session takes place on the same day or a different day than the previous therapy session. In this embodiment, the pressure provided to the patient is incremented by a predetermined amount Δp, or is increased continuously as discussed in greater detail below, after a predetermined number n of therapy sessions have elapsed. If the pressure is to be increased after each therapy session, for example, n is set to one. Typically, a therapy session is considered to have taken place if the pressure support system is turned on and back off again after some minimum amount of time has elapsed.

Yet another embodiment of the present invention contemplates incrementing the therapy pressure $P_{current}$ based on the number of hours that the pressure support system is in use. In effect, in this embodiment the predetermined number n corresponds to the number of hours the unit has been operating so that once an predetermined number n of hours have elapsed, the pressure to the patient is increased. This increase can take place immediately, preferably by slowing increasing the pressure the predetermined amount, or the pressure increase can take place in the next therapy session.

Figure 6A:
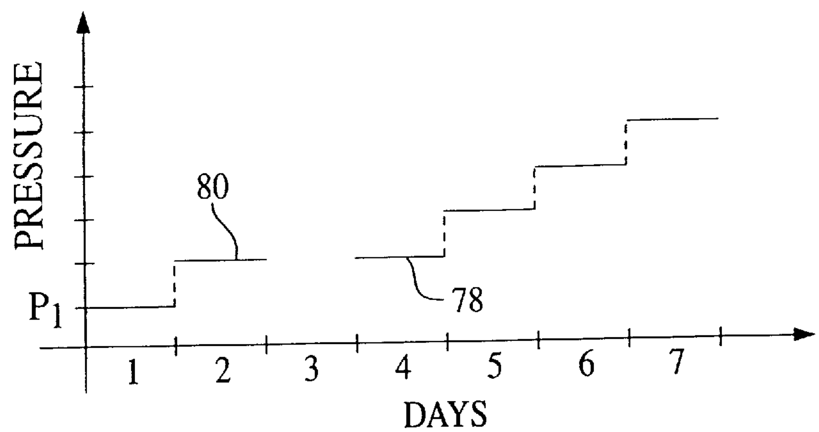
FIGS. 6A–6C, 7, 8 and 9 are additional waveforms illustrating examples of the pressure changes provided by the pressure support system of the present invention.
Figure 6B:
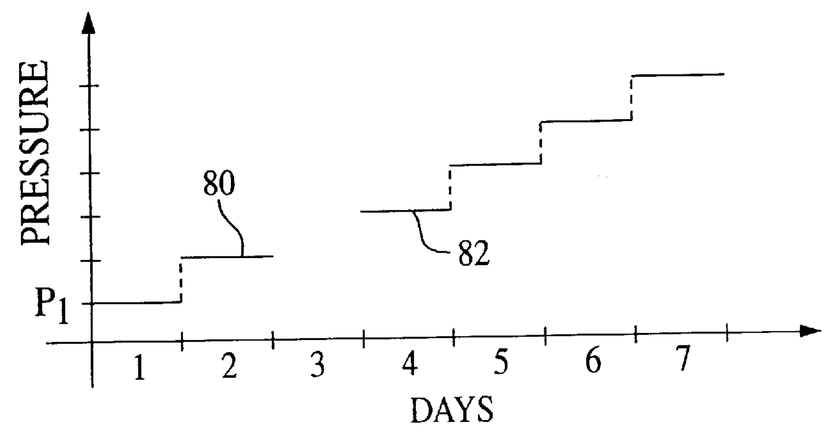
Figure 6C:
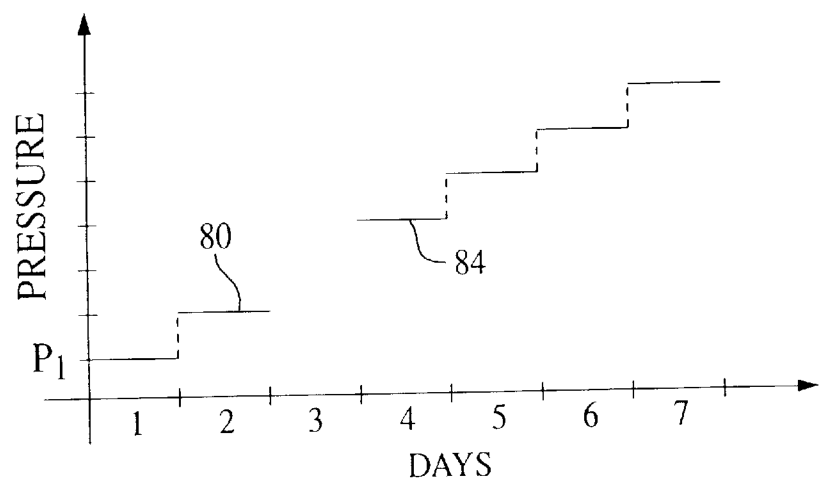

The present invention also recognizes that there may be instances when the patient fails to comply with the treatment regimen and skips one or more of the daily therapy sessions. FIGS. 6A–6C are waveforms illustrating examples of the pressure versus days curves provided by the pressure support system of the present invention in the event that a therapy session is missed. In each of these figures, it is assumed that the patient failed to perform the therapy session that would otherwise take place on day 3.

In one embodiment of the present invention shown in FIG. 6A, the pressure level 78 in the therapy session on the fourth day is the same as the pressure level 80 in the therapy session on the second day, which is the day of the last therapy session. Thus, if the patient misses a therapy session, the pressure support system resumes the pressure provided to the patient at the level of the last therapy session.

It is to be understood that in this embodiment, if the total number of days D remains unchanged, the pressure level at the end of D days will not equal the set final pressure $P_2$, but will be reduced by two incremental amounts due to (1) the missed therapy session (day 3) and (2) the fact that the pressure provided on day 4 is the same as the last pressure level. Thus, on the final day D, the current pressure will be two pressure level increments below where it would have been had that patient not missed the therapy session. To account for this discrepancy, the present invention contemplates incrementing the total number of days D by 2 for each day missed in order to reach the final pressure $P_2$. Alternatively, if D is to remain unchanged, the present invention contemplates recalculating incremental amount $\Delta p$ by subtracting a current pressure 78 from the final pressure $P_2$ and dividing a result by a number of days remaining (D-N) until the first predetermined number of days D is reached. The result will be an increase in the incremental amount $\Delta p$, but the final pressure $P_2$ will be reached in the set number of days D.

In another embodiment of the present invention shown in FIG. 6B, the pressure level 82 in the therapy session on the fourth day corresponds to the pressure level 80 in the therapy session on the second day, which is the day of the last therapy session, increased by one incremental amount $\Delta p$. Thus, if the patient misses a therapy session, the pressure support system provides the continuous flow of breathing gas to the patient at the pressure level that the patient would have received on the day missed. As in the previous embodiment, if the total number of days D remains unchanged, the pressure level at the end of D days will not equal the set final pressure $P_2$, but will be reduced by one incremental amount due to the missed therapy session (day 3). To account for this discrepancy, the present invention contemplates incrementing the total number of days D by 1 for each day missed in order to reach the final pressure $P_2$. Alternatively, if D is to remain unchanged, the present invention contemplates recalculating incremental amount $\Delta p$ by subtracting a current pressure 82 from said final pressure $P_2$ and dividing a result by a number of days remaining (D-N) until said first predetermined number of days D is reached. As in the previous embodiment, the result will be an increase in the incremental amount $\Delta p$, but the final pressure $P_2$ will be reached in the set number of days D.

In yet another embodiment of the present invention shown in FIG. 6C, the pressure level 84 in the therapy session on the fourth day corresponds to the pressure level 80 in the therapy session on the second day, which is the day of the last therapy session, increased by two incremental amount $\Delta p$. Thus, if the patient misses a therapy session, the pressure support system provides the continuous flow of breathing gas to the patient at the pressure level that the patient would have received had the day/therapy session not missed. In effect, the pressure support system ignores the fact that the patient did not receive a pressure support therapy on day three and outputs a pressure on day four as if the patient did receive the therapy on day three. Unlike the previous embodiments, neither the total number of days D nor the incremental amount $\Delta p$ need to be readjusted to account for the missed therapy session.

It is to be understood that other conventional techniques for controlling the pressure and flow of the flow of breathing gas provided to the patient during a single therapy session can be used in conjunction with the automatic, gradual, daily pressure increasing regimen of the present invention. For example, it is known to provide one or more ramp cycles in which the continuous flow of breathing gas in a single therapy session is initially provided at a low level and increases to the current pressure $P_{current}$ over a period of time. This period of time can be measured by a clock or based on the number of respiratory cycles of the patient. This conventional ramp cycle allows the patient time to fall asleep under a relatively low pressure level.

Figure 7:
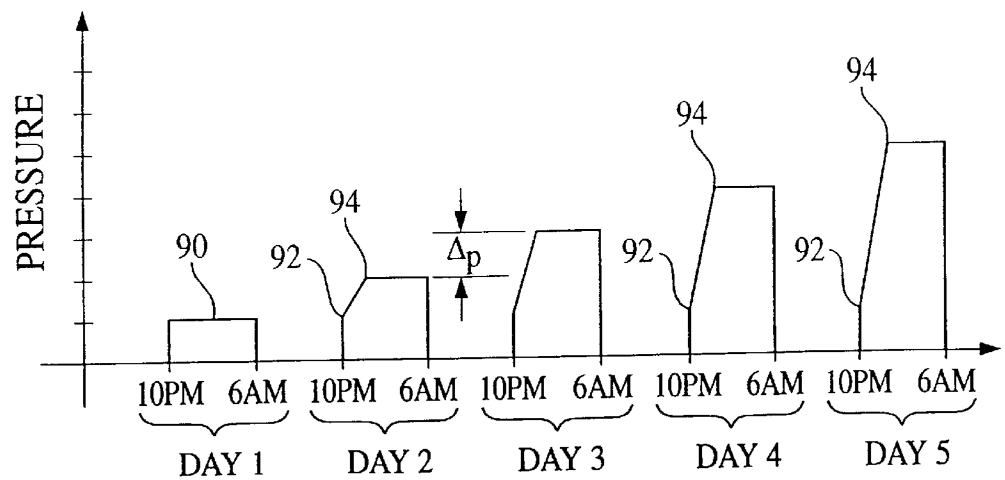

FIG. 7 illustrates a pressure curve 90 showing the pressure provided to the patient over a number days, where 1) the therapy pressure, i.e., the current pressure $P_{current}$, to be provided to the patient, increases by an amount $\Delta p$ each day, and 2) the instantaneous pressure provided to the patient during the course of each therapy session, i.e., each day, is ramped from a low pressure 92 to the therapy pressure 94, $P_{current}$, for that day. For the sake of illustration, the therapy sessions shown in FIG. 7 are considered to begin at 10:00 pm and last until 6:00 am the next morning. For example, the present invention contemplates initiating the therapy at a pressure of 2 $cmH_2O$ at the start of each therapy session with a 20 minute ramp from the initial pressure of 2 cm $H_2O$ to the therapy pressure for that day. If the therapy pressure, i.e., the current pressure, $P_{current}$ to be provided to the patient during that session is 2 $cmH_2O$, no ramp function is performed. This is show by viewing pressure curve 90 for day 1 in FIG. 7. In later therapy sessions, however, as the daily therapy pressure is increase by the predetermined amount $\Delta p$, a ramping of the pressure from initial pressure 92 to the therapy pressure 94 ($P_{current}$) takes place.

It can be appreciated that as the daily therapy pressure, $P_{current}$, increases, the slope of the individual ramp functions will likewise increase, assuming the duration of these ramp functions remain unchanged. The present invention contemplates also controlling the duration of the individual ramp functions over the course of the therapy sessions to maximize the comfort of the patient during each therapy session. For example, the duration of the ramp function provided at the outset of each therapy session can be increased as the number of therapy sessions increase to ensure that the patient is not presented with too rapid of an increase in pressure during the period of the ramp.

Figure 8:
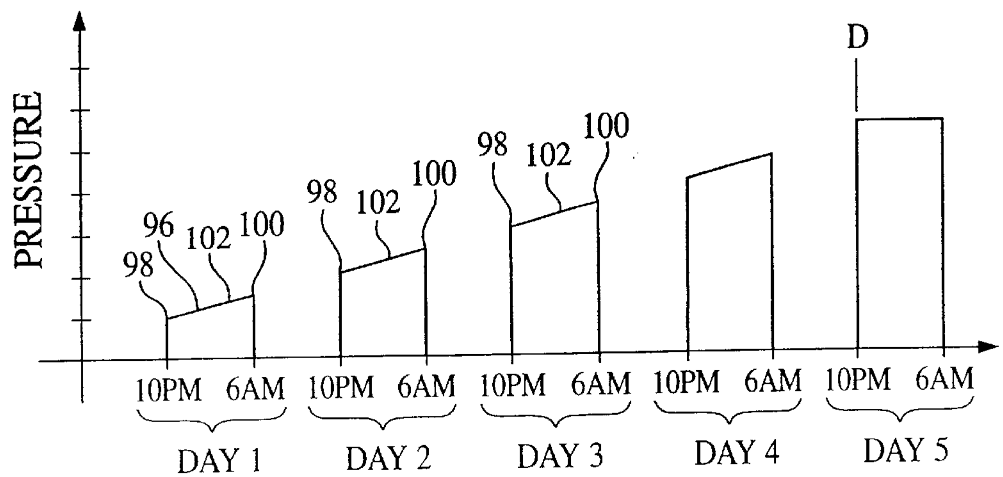

In the previous embodiments, the pressure provided to the patient is incremented by a predetermined discrete amount Δp after a certain period of time n or after n therapy sessions. However, the present invention also contemplates continuously, rather than incrementally, increasing the therapy pressure, $P_{current}$, provided to the patient during a therapy session. As in the previous embodiments, this continuous increase can take place of over a number of days D or until a final therapy pressure $P_2$ is reached. FIG. 8 illustrates an example of such a continuous increase in the current therapy pressure.

Curve 96 in FIG. 8 represents the pressure provided to the patient over a number of days. More specifically, 5 days are shown in this figure. In each therapy session (days 1–5), the therapy pressure 98 at the start of the therapy session is lower than the therapy pressure 100 at the end with the instantaneous therapy pressure 102, $P_{current}$, increasing continuously during each therapy session. As shown, the therapy pressure increases over a number of days in a relatively linear fashion. The present invention, contemplates, however, that this increase need not be linear. Instead, as with the previous embodiments, the multiple-day pressure increase can be, for example, exponential, parabolic or sinusoidal shaped.

Figure 9:
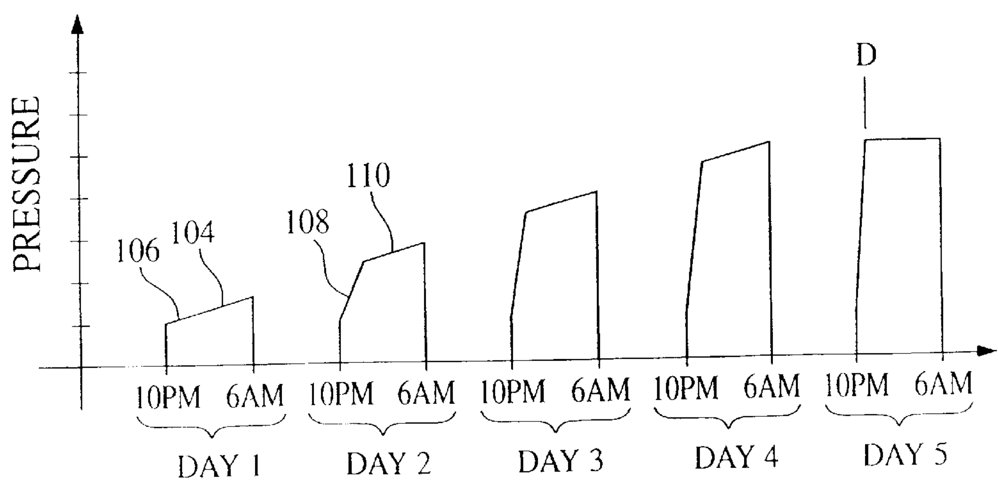

It can be appreciated that the above-described individual ramp functions, where the pressure during each therapy session is ramped from an initial relatively low level to the therapy pressure, $P_{current}$, can be combined with the embodiment of the present illustrated in FIG. 8, where the therapy pressure, $P_{current}$, is itself increasing over a number of days D. FIG. 9 illustrates a pressure curve 104 showing such a combination, which is essentially a combination of the pressure curves from FIGS. 7 and 8. As shown in FIG. 9, in each therapy session, except for the initial therapy session 106, the pressure curve provided to the patient has two distinct portions. First portion 108 corresponds to a pressure ramp of FIG. 7, which is provided at the onset of each therapy session, where the pressure is first provided at a low level and increases toward the final therapy pressure, $P_{current}$, so that the patient has time to fall asleep under a relatively low pressure. Second portion 110 corresponds to the therapy pressure $P_{current}$, which, in this embodiment, is itself increasing as discussed above with respect to FIG. 8.

A further embodiment of the present invention contemplates providing a "reverse" ramp cycle beginning near the end of the therapy session so that the pressure level decreases from the current pressure level to a final low pressure level so that near the time the patient is waking up, he or she is not being provided the relatively higher $P_{current}$ it pressure level. It is also known to delay providing the pressure to the patient altogether for some period of time. In addition, a reset function can be provided, which, when activated, immediately reduces the pressure provided to the patient. After a suitable reset period, the pressure provided to the patient resumes at the level it was at prior to the reset, the operating level $P_{current}$ or another ramp function can be implemented.

The present invention contemplates that other conventional functions associated with pressure support therapies can be provided in the breathing gas delivery system of the present invention. Examples of such functions include an automatic ON/OFF feature where the system turns on when the patient interface is donned by the patient and turns off when it is removed; minimum system leakage assurance that provides a relative high pressure at the start of the treatment for a short duration (either timed or based on breath count) to allow the user to adjust the patient interface device to reduce leaks; and a therapy delay function that delays operation of the unit for some duration, which can be timed or based on breath count. These and other functions are described in U.S. Pat. Nos. 5,239,995; Re. 35,295; 5;492,113, 5,551,418; and 5,823,187 all to Estes et al., the contents of which are incorporated herein by reference, and in U.S. Pat. No. 5,117,819 to Servidio et al., the contents of which is also incorporated herein by reference.

With the growing popularity of managed healthcare, healthcare providers are becoming more concerned that the patients actually use the prescribed therapy devices. To meet this concern, the present invention also contemplated monitoring patient compliance by monitoring and storing information regarding the use of the pressure support system, such as the amount of time that the unit was turned on and/or the amount of time patient respiratory cycles where detected, which can be done using any conventional technique. This information can be displayed on the input/output device and/or download for review by the caregiver using any conventional technique, including downloading data via the internet, a modem, satellite communication, telephone communication (cellular and/of landlines), and a physical exchange of a storage medium containing the compliance information.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A pressure support system comprising:

a gas flow generating system adapted to generate a continuous flow of breathing gas at selectable pressures;

a patient circuit having a first end coupled to an output of said gas flow generating system to communicate said continuous flow of breathing gas to a patient;

a patient interface coupled to a second end of said patient circuit to communicate said continuous flow of breathing gas from said patient circuit to an airway of a patient;

usage tracking means for monitoring usage of the pressure support system by a patient;

a controller operatively coupled to said usage tracking means and said gas flow generating system, wherein said controller outputs a control signal to said gas flow generating system to control said gas flow generating system, wherein said controller determines whether such a patient has completed a therapy session based on an output of said usage tracking means, and wherein said controller causes said gas flow generating system to provide said continuous flow of breathing gas to such a patient at a first pressure $P_1$ in an initial therapy session and increases said pressure of said continuous flow of breathing gas from said first pressure $P_1$ to a final pressure $P_2$ over a first predetermined number D of therapy sessions, so that a current pressure $P_{current}$ of said continuous flow of breathing gas provided to a patient in a current therapy session following said initial therapy session is greater than a pressure provided to such a patient in a previous therapy session.

2. A pressure support system according to claim 1, wherein said controller increases said pressure of said continuous flow of breathing gas from said first pressure $P_1$ to said final pressure $P_2$ over said first predetermined number D of therapy sessions by causing said gas flow generating system to increase said pressure of said flow of breathing gas by a predetermined incremental amount Δp after every n therapy session(s) over said first predetermined number D of therapy sessions.

3. A pressure support system according to claim 2, wherein n is equal to one, so that an increase in said pressure of said continuous flow of breathing gas provided to a patient by said predetermined amount Δp from said first pressure to said final pressure occurs after such a patient completes each therapy session following said initial therapy session.

4. A pressure support system according to claim 2, wherein said controller causes said gas flow generating system to output said continuous flow of breathing gas at a constant pressure during a major portion of a therapy session.

5. A pressure support system according to claim 2, wherein said controller automatically determines said predetermined amount Δp by subtracting said first pressure $P_1$ from said final pressure $P_2$ and dividing a result by said first predetermined number D of therapy sessions.

6. A pressure support system according to claim 2, wherein said controller causes said gas flow generating system to output said continuous flow of breathing gas at (1) a pressure of a last therapy session or (2) a pressure of a last therapy session increased by said predetermined incremental amount Δp responsive to said controller determining that a therapy session was not completed on a preceding day.

7. A pressure support system according to claim 6, wherein said controller also increments said first predetermined number D of therapy sessions by one if a therapy session was not completed on a preceding day.

8. A pressure support system according to claim 6, wherein said controller recalculates said predetermined incremental amount Δp by subtracting a current pressure from said final pressure $P_2$ and dividing a result by a number of therapy sessions remaining until said first predetermined number D of therapy sessions is reached, if a therapy session was not completed on a preceding day.

9. A pressure support system according to claim 1, wherein said controller increases a pressure of said continuous flow of breathing gas from said first pressure $P_1$ to said final pressure $P_2$ over said first predetermined number D of therapy sessions by causing said gas flow generating system to increase a pressure of said flow of breathing gas by a predetermined incremental amount Δp after n therapy sessions over a first predetermined number of days.

10. A pressure support system according to claim 1, wherein said controller increases a pressure of said continuous flow of breathing gas from said first pressure $P_1$ to said final pressure $P_2$ over said first predetermined number D of therapy sessions by causing said gas flow generating system to increase said current pressure $P_{current}$ of said flow of breathing gas on a continuous basis during operation of said pressure support system.

11. A pressure support system according to claim 1, wherein said controller determines a therapy start date of said initial therapy session and, at each subsequent therapy session, said controller determines a number of days that have elapsed since said therapy start date and sets a pressure at which said continuous flow of breathing gas is to be provided to said patient during a current therapy session based on said number of days elapsed since said therapy start date.

12. A pressure support system according to claim 1, wherein, in a therapy session, said controller causes said gas flow generating system to output said continuous flow of breathing gas at an initial low pressure and increases said pressure to said current pressure $P_{current}$ over a period of time.

13. A pressure support system according to claim 1, wherein said gas flow generating system includes:

a flow generator that outputs a substantially constant predetermined flow of breathing gas; and a breathing gas pressure controller operatively coupled to said flow generator and said controller, wherein said breathing gas pressure controller varies a pressure of the flow of breathing gas output from said flow generator based on an output from said controller to provide said flow of breathing gas at a selected pressure.

14. A pressure support device comprising:

gas flow generating means for providing a continuous flow of breathing gas at selectable pressure levels;

means for communicating said continuous flow of breathing gas to an airway of a patient;

usage tracking means for monitoring usage of the pressure support device by a patient;

control means for determining whether such a patient has completed a therapy session based on an output of said usage tracking means and for causing said gas flow generating means to provide said continuous flow of breathing gas to such a patient at a first pressure $P_1$ in an initial therapy session and to increase said pressure of said continuous flow of breathing gas from said first pressure $P_1$ to a final pressure $P_2$ over a first predetermined number D of therapy sessions so that a current pressure $P_{current}$ of said continuous flow of breathing gas provided to a patient in a current therapy session following said initial therapy session is greater than a pressure provided to such a patient in a previous therapy session.

15. A pressure support device according to claim 14, wherein said control means increases a pressure of said continuous flow of breathing gas provided to said patient in subsequent therapy sessions until the final pressure level $P_2$ is reached or a number of days D elapse.

16. A pressure support device according to claim 14, wherein said control means increases a pressure of said continuous flow of breathing gas from said first pressure $P_1$ to said final pressure $P_2$ over said first predetermined number D of therapy sessions by causing said gas flow generating means to increase a pressure of said flow of breathing gas by a predetermined incremental amount Δp after every n therapy sessions over said first predetermined number D of therapy sessions.

17. A pressure support device according to claim 16, further comprising input/output means for entering said first pressure $P_1$, said final pressure $P_2$, and said number D of therapy sessions, wherein said control means sets said predetermined amount Δp as follows: $\Delta p=(P_2-P_1)/D$.

18. A pressure support device according to claim 16, wherein said control means sets a current pressure $P_{current}$ provided to a patient in a therapy session subsequent to said initial therapy session as follows: $P_{current}=\Delta p*N+P_1$, where N is an integer corresponding to a number of therapy sessions that have been completed since said initial therapy session.

19. A pressure support device according to claim 16, wherein said control means causes said gas flow generating means to output said continuous flow of breathing gas at (1) a pressure level of a last therapy session or (2) a pressure level of a last therapy session increased by said predetermined incremental amount $\Delta p$ responsive to said controller determining that a therapy session was not completed on a preceding day.

20. A pressure support device according to claim 14, wherein said control means increases said pressure of said continuous flow of breathing gas from said first pressure $P_1$ to said final pressure $P_2$ over said first predetermined number D of therapy sessions by causing said gas flow generating system to increase said pressure of said flow of breathing gas by a predetermined incremental amount $\Delta p$ after n therapy sessions over said first predetermined number D of therapy sessions.

21. A pressure support system according to claim 20, wherein n is equal to one so that an increase in said pressure of said continuous flow of breathing gas provided to a patient by said predetermined amount $\Delta p$ from said first pressure to said final pressure occurs after such a patient completes each therapy session following said initial therapy session.

22. A pressure support device according to claim 14, wherein said control means increases a pressure of said continuous flow of breathing gas from said first pressure $P_1$ to said final pressure $P_2$ over said first predetermined number D of therapy sessions by causing said gas flow generating system to increase a current pressure $P_{current}$ of said flow of breathing gas on a continuous basis during operation of said pressure support device.

23. A pressure support device according to claim 14, wherein, in a therapy session, said control means causes said gas flow generating system to output said continuous flow of breathing gas at an initial low pressure and increases said pressure to a current pressure over a period of time, wherein said period of time is measured by one of a clock source and a respiratory count of a patient.

24. A method of providing pressure support to a patient, comprising:

(a) providing a continuous flow of breathing gas to a patient at a first pressure $P_1$ in an initial therapy session by means of a gas flow generating system that operates under control of a controller based on a control signal provided to said gas flow generating system by said controller;

(b) determining whether a patient has completed a therapy session in which such a patient receives said flow of breathing gas for a predetermined period of time;

(c) increasing said pressure of said continuous flow of breathing gas from said first pressure $P_1$ to a final pressure $P_2$ over a first predetermined number D of therapy sessions so that a current pressure $P_{current}$ of said continuous flow of breathing gas provided to a patient in a current therapy session following said initial therapy session is greater than a pressure provided to such a patient in a previous therapy session responsive to such a patient having completed a therapy session; and (d) repeating step (c) until the final pressure level $P_2$ is reached or a predetermined number D of therapy sessions elapse.

25. A pressure support system according to claim 24, wherein said increasing step includes increasing a pressure of said continuous flow of breathing gas from said first pressure $P_1$ to said final pressure $P_2$ over said first predetermined number D of therapy sessions by causing said gas flow generating system to increase a pressure of said flow of breathing gas by a predetermined incremental amount $\Delta p$ after every n therapy sessions over said first predetermined number D of therapy sessions.

26. A method according to claim 25, further comprising manually entering said first pressure level $P_1$, said final pressure level $P_2$, and said first predetermined number D of therapy sessions to said controller, and wherein said controller automatically calculates said predetermined amount $\Delta p$ as follows: $\Delta p=(P_1-P_1)/D$.

27. A method according to claim 25, wherein said step (c) includes setting a current pressure $P_{current}$ provided to a patient in a therapy session as follows: $P_{current}=\Delta p*N+P_1$, where N is an integer corresponding to a number of therapy sessions since said initial therapy session.

28. A method according to claim 25, further comprising providing said continuous flow of breathing gas at (1) a pressure level of a last therapy session or (2) a pressure level of a last therapy session increased by said predetermined incremental amount $\Delta p$ responsive to said controller determining that a therapy session was not completed on a preceding day.

29. A method according to claim 24, wherein said step (c) includes outputting said continuous flow of breathing gas at an initial low level and increasing said pressure to a current therapy level over a period of time, wherein said period of time is measured by one of a clock source and a respiratory count of a patient.

30. A method according to claim 24, wherein said increasing step includes increasing a pressure of said continuous flow of breathing gas from said first pressure $P_1$ to said final pressure $P_2$ over said first predetermined number D of therapy sessions by causing said gas flow generating system to increase a current pressure $P_{current}$ of said flow of breathing gas on a continuous basis during operation of said pressure support system.

* * * * *

UNITED STATES PATENT AND TRADEMARK OFFICE

CERTIFICATE OF CORRECTION

PATENT NO. : 6,401,713 B1
DATED : June 11, 2002
INVENTOR(S) : Hill et al.

It is certified that error appears in the above-identified patent and that said Letters Patent is hereby corrected as shown below:

Column 16,
Line 9, change “pressure support system” to -- method --

Signed and Sealed this

Fourth Day of November, 2003

JAMES E. ROGAN
*Director of the United States Patent and Trademark Office*